United States Patent [19]

Wille

[11] Patent Number: 5,716,987
[45] Date of Patent: Feb. 10, 1998

[54] PROPHYLACTIC AND THERAPEUTIC TREATMENT OF SKIN SENSITIZATION AND IRRITATION

[75] Inventor: John J. Wille, Trenton, N.J.

[73] Assignee: Bristol-Myers Squibb Company, New York, N.Y.

[21] Appl. No.: 670,201

[22] Filed: Jun. 21, 1996

[51] Int. Cl.$^6$ .......................... A61K 31/235; A61K 31/19
[52] U.S. Cl. ................................. 514/543; 514/557
[58] Field of Search ........................ 514/557, 543

[56] References Cited

PUBLICATIONS

Embase Abstract 93170262, 1992. Cossel et al.

*Primary Examiner*—Zohreh Fay
*Attorney, Agent, or Firm*—Theodore R. Furman, Jr.; John M. Kilcoyne

[57] ABSTRACT

Methods, compositions and systems for preventing an adverse reaction of the skin to the presence of a skin-sensitizing and/or skin-irritating agent by administering an effective amount of phenoxyacetic acid and/or a lower alkyl ester thereof to a warm blooded animal.

17 Claims, No Drawings

5,716,987

PROPHYLACTIC AND THERAPEUTIC TREATMENT OF SKIN SENSITIZATION AND IRRITATION

FIELD OF THE INVENTION

The present invention relates to methods and compositions for preventing adverse reactions of the skin to skin-sensitizing or skin-irritating agents.

BACKGROUND OF THE INVENTION

The skin is susceptible to penetration by agents that sensitize the skin or irritate the skin. As used herein the term "skin-sensitizing agent" is a substance that generally causes the formation of memory cells which recognize future contact with the sensitizing agent. Such future contact can result in an adverse reaction, both locally and at remote sites on the body. In general, a "skin-irritating agent" is a substance (e.g. soap) that causes an immediate and generally localized adverse response. The response is typically in the form of redness and/or inflammation and does not extend beyond the immediate area of contact nor does it cause the formation of memory cells. As used herein, the term "adverse skin reaction preventing or treating agent" shall mean collectively agents used in the present invention against skin-sensitizing agents and/or skin-irritating agents.

Allergic reactions of the skin to skin-sensitizing agents, known as allergic contact dermatitis (ACD), are immune responses that occur in the skin. The response is the result of the penetration of the skin by a foreign substance (e.g. hapten or antigen) that provokes a skin sensitization reaction. ACD is a two phase process involving an initial induction phase followed by an elicitation phase.

The induction phase occurs immediately after first time exposure of the skin to the hapten or antigen and is characterized by the formation of immune memory cells that can subsequently recognize the specific hapten or antigen which previously entered the skin for the first time.

The elicitation phase occurs when the skin is subsequently re-exposed to the original hapten or antigen. In the elicitation phase, the skin provides an overt reaction to the presence of the hapten or antigen in the form of a skin inflammatory response.

ACD generally results in a life-time persistent memory for the specific hapten or antigen. Thus, when the skin is exposed to the hapten or antigen at a subsequent time, there is typically an immediate and often severe skin inflammatory response.

Agents that cause allergic contact dermatitis are varied and numerous and include, for example, metals (e.g. nickel, chromium, cobalt and the like) fragrances, chemicals, cosmetics, textiles, pesticides, plastics, pollen and the like (see, for example, R. J. G. Rycroft et al. "Textbook of Contact Dermatitis"). Therapeutic agents such as drugs may also cause allergic contact dermatitis particularly when administered transdermally.

Transdermal delivery of drugs provides many advantages over alternate routes of administration. Transdermal delivery systems (TDS) for delivery of drugs or other beneficial agents are well-known (see, for example, U.S. Pat. Nos. 3,598,122, 3,598,123, 4,286,592, 4,314,557, 4,379,454, 4,599,222 and 4,573,995, which are each incorporated herein by reference). A TDS is generally composed of the following components: (a) "basic components", including backing, matrix reservoir, and an optional separate adhesive layer; (b) the drug or other therapeutic agent; (c) "additives", including solubilizers, plasticizers and permeation enhancers; and (d) "impurities" such as residual amounts of monomers, initiators, cross-linkers, etc., from the polymerization process during fabrication of the basic components.

The conditions under which TDS are administered are highly conducive to the induction of skin allergic reactions, and the following skin reactions may be expected to occur:

1. Irritant reactions to the drug, an additive, an impurity, or a combination thereof;
2. Allergic reactions, especially to the low molecular weight components (drug, additive, impurity, adhesive);
3. Local sweat retention syndrome resulting from prolonged skin occlusion which causes blocking of sweat ducts.

Allergic contact dermatitis presents a significant problem in the transdermal administration of therapeutic agents. It is well known that many drugs, including some currently marketed in the United States (e.g. clonidine) sensitize the skin when used in a transdermal delivery system. Skin sensitization may be produced not only by the transdermally delivered drug, but also by a non-sensitizing drug combined with skin sensitizing permeation enhancers, or a combination of a sensitizing drug and a sensitizing permeation enhancer. Penetration of these sensitizing agents into the skin and the resulting adverse reaction of the skin may persist well beyond the time that the transdermal patch is removed from the skin. The reaction of the skin may be a source of discomfort and a clinical complication in a patient suffering from such a reaction.

Unlike the response induced by skin-sensitizing agents, the non-allergic response to skin-irritating agents is immediate and localized and does not invoke activation of the immune system through the production of immune memory cells.

The most common response associated with skin-irritating agents is the onset of inflammation. The main steps of the inflammatory response include, the neurologic phase, the vascular phase and the cellular phase. In the neurologic phase transient vasoconstriction occurs typically within about 30 seconds of contact with the skin-irritating agent. Within about one to six minutes of contact, vasodilation occurs followed by the margination of neutrophils in the vessels and diapedesis, the outward passage of corpuscular elements through intact vessel walls.

The non-immune response to a skin-irritating agent is the result of a substance that causes direct toxic damage to the skin without preceding allergic sensitization. The response to contact is dependent upon the nature of the skin, the skin-irritating agent, its concentration, the situs of contact on the body and environmental factors such as humidity and temperature. Examples of potential skin-irritating agents include water, skin cleansers, industrial cleaning agents, alkalis, acids, oils, organic solvents, oxidizing agents, reducing agents, plant matter, animal matter, combinations thereof and the like.

Efforts have been made to address the problem of allergic contact dermatitis by prophylactically treating the skin to prevent the onset of the induction phase of ACD and/or to therapeutically prevent or reduce the adverse effects of the elicitation phase of ACD. For example, U.S. Pat. No. 5,202,130 discloses that lanthanide ions and organic calcium channel blockers individually can be used for the treatment of contact allergic dermatitis.

Wolfgang Diezel et al., *J. Invest. Derm.*, Vol. 93, No. 3, pp. 322–326 (September 1989) discloses the sensitization of mice with 1-chloro-2, 4-dinitrobenzene and subsequent treatment with lanthanum citrate and diltiazem hydrochloride to prevent the onset of the induction phase of the sensitizing agent. Philip W. Ledger, et al., U.S. Pat. No. 5,120,545 disclose the prevention of skin sensitization by the administration of an antigen processing-inhibiting agent such as ammonium chloride. A method of preventing contact sensitization using steroids (e.g. corticosteroid and glucocorticoid carboxylic acid esters) is disclosed, for example, in Alfred Amkraut, U.S. Pat. No. 5,118,509 and Peter M. Ross, et al., U.S. Pat. No. 4,897,260.

A method of reducing the adverse effects of administering a sensitizing or irritating drug by using methyl nicotinate is disclosed in Michel Cormier et al., U.S. Pat. No. 5,451,407.

Methods of treating ACD through the blocking of the elicitation phase after initial exposure to a drug is disclosed, for example, in John McFadden, et al., *J. Invest. Derm.*, Vol. 99, No. 6, pp. 784-786 (December 1992). Tuberculin-induced delayed- type hypersensitivity reaction in human skin was inhibited by topical application of verapamil hydrochloride prior to or concurrent with challenge with tuberculin.

Also, Richard L. Gallo, et al., *Arch. Dermatol.*, Vol. 125, pp. 502-506 (April 1989) discloses the administration of the diuretic amiloride hydrochloride as a topical anti-inflammatory agent in the treatment of ACD, particularly mice sensitized with 2,4,6-trinitrobenzene.

As disclosed in commonly assigned U.S. application Ser. No. 08/198,003 filed Feb. 17, 1994, and references cited therein, irradiation of skin with ultraviolet light B (UVB) is known to be immunosuppressive. These UVB effects are thought to be mediated, in part, by the UVB-induced isomerization of trans-urocanic acid (trans-UCA), a molecule which makes up about 0.5% of the total dry weight in the upper layers of human epidermis, to cis-urocanic acid (cis-UCA). Cis-UCA is known to have various immunosuppressive actions in vivo in a number of experimental systems and is believed to act through histamine-like receptors in the skin. More recently, it has been shown that the UVB impairment of the induction phase of allergic contact dermatitis to epicutaneously applied haptens in certain mouse strains depended on the participation of the cytokine, tumor necrosis factor-a (TNFa). It has been suggested that local release of TNFa may inhibit sensitization by trapping epidermal Langerhans cells and preventing them from reaching the draining lymph node where they activate T. cells.

As further disclosed in U.S. application Ser. No. 08/198, 003, mast cell degranulators such as cis-urocanic acid are effective for preventing or inhibiting the skin sensitizing effect of a transdermally administered therapeutic agent.

Hand eczema is a common clinical condition treated and evaluated by dermatologists. There are thought to be two principal causes of eczema, although typically eczema is caused by a combination of factors. One factor is atopic dermatitis, a multifactorial genetic disorder. Atopic dermatitis is common in children, affecting 3% of all infants. Remissions are frequent in childhood, but the eczema is likely to recur as a chronic disease in adulthood. Other factors include external irritants (chemical/physical); contact allergy; infection; venous stasis; scratching; sweating; autosensitization and stress. The treatment of eczema has been made easier by the introduction of topical steroids.

Over the past ten years, research has uncovered many epidemiological and risk factors related to specific environmental exposures. In particular, health care professionals suffer persistent irritation from the frequent use of medicated hand washes attributable to active agents in the formulations, such as surfactants (e.g., sodium lauryl sulfate), and/or the effects of repeated wetting and drying of hands.

The use of oxidative dyes, e.g., p-phenylenediamine in hair coloring salons as well as other hair conditioning products may result in both skin irritation and sensitization reactions among a susceptible segment of users and hair care professionals. Finally, there are many otherwise safe topical medicaments that contain active ingredients (e.g., retinoic acid, lactic acid, capsaicin and topical non-steroidal anti-inflammatory drugs (NSAID)) used in sports medicine, for treatment of the rheumatic and skeleto-muscular pains, and for anti-aging and the like that cause skin irritation and sensitization reactions in some fraction of treated patients.

Topical steroids and non-steroidal anti-inflammatories have been proposed for the therapeutic treatment of eczema. However, such agents, often obtained only with a prescription, cannot be added to medicaments and skin care products to prevent skin irritation and skin sensitization due to the active ingredients contained therein.

Despite these efforts and the knowledge gained regarding the cause of ACD, there remains a need to develop compositions which effectively prevent the onset of ACD or reduce the adverse affects of ACD after the person has been sensitized to an agent, as for example, a transdermally administered agent such as a drug or agents contained within commercial products such as hair lotions and the like which can cause ACD. There is likewise the need to develop compositions which effectively prevent reactions to skin-irritating agents.

Applicants have gained the knowledge that there is a distinct process step implicated in the immune response associated with allergic contact dermatitis, which when interfered with, results in the prevention and/or treatment of ACD. This process step referred to herein as cellular signal transduction, is believed responsible for the acquisition of memory by T-lymphocytes, for the cytokine-mediated regulation of antigen presentation and for other cellular processes as well. Applicants have discovered that lower alkyl esters of phenoxyacetic acid interferes with cellular signal transduction and therefore can be used to prevent or treat allergic contact dermatitis.

Applicants have also discovered that phenoxyacetic acid and lower alkyl esters of phenoxyacetic acid when administered in appropriate amounts, alone or as part of commercial products (e.g. hair lotions), achieve significant improvement in the desensitization of a patient's skin and prevent inflammation of the skin including the symptoms associated with eczema. As a result, the reaction of the skin to skin-sensitizing agents or skin-irritating agents is better controlled. The present invention therefore provides prevention of an adverse reaction to the skin.

SUMMARY OF THE INVENTION

The present invention is generally directed to methods of preventing allergic contact dermatitis (ACD) and/or skin irritation including eczema and compounds, compositions and systems to accomplish the same. In one aspect of the invention a method is provided for preventing an adverse reaction of the skin caused by the presence of skin-sensitizing agents such as therapeutic agents (e.g. drugs) metals, fragrances, cosmetics, hair preparations, textiles, pollen, pesticides, plastics, combinations thereof and the like, or skin-irritating agents such as cleansers, cleaning agents, alkalis, acids, oils and the like.

The present invention is also applicable to ACD induced by the transdermal administration of an agent, as for example, a therapeutic agent such as a drug. In general, the present invention includes a method of preventing an adverse reaction of the skin to the presence of at least one of a skin-sensitizing agent and skin-irritating agent including eczema comprising administering to a said warm-blooded animal an effective amount of an adverse skin preventing agent comprising phenoxyacetic acid and lower alkyl esters thereof having the Formula (1)

wherein R is hydrogen or a lower alkyl group. Lower alkyl as defined herein shall include straight and branched chain alkyl groups having from 1 to 6, preferably from 1 to 4 carbon atoms. The preferred group for R is methyl. Ph is a phenyl group.

The skin-sensitizing or skin-irritating agents employed in the present invention can be prepared in the form of a composition containing one or more additives including skin permeation enhancers, excipients and the like.

The adverse skin reaction preventing agents of the present invention may be administered topically in the form of lotions, creams, sprays and the like, by non-cutaneous routes as well as through the use of transdermal patches. In transdermal applications, the agents may be administered from a single reservoir also containing a therapeutic agent or preferably from a separate reservoir of a transdermal patch.

In addition the agents of the present invention may be added to conventional products which are applied to or come into contact with the skin such as hair treatments (e.g. shampoos, conditioners and the like), skin lotions, cream, salves and the like.

DETAILED DESCRIPTION OF THE INVENTION

The present invention is in part directed to methods and systems for preventing the onset of skin sensitization reactions caused by allergic contact dermatitis by treatment before, after or during the induction phase of sensitization and for alleviating this condition once ACD has progressed to the elicitation phase. In one aspect of the invention the skin is treated with a compound selected from phenoxyacetic acid and lower alkyl esters thereof alone or as part of a product which is applied to or contacts the skin. Such products include, but are not limited to, anti-aging compositions (e.g. retinoids and alpha-hydroxy acids), hair treatment preparations such as shampoos and conditioners, soaps whether in liquid or solid form, detergents, perfumes, cosmetics, household and industrial cleaners, organic solvents and the like. Such products can be in the form of liquids, lotions, creams, gels, salves, suspensions, emulsions and the like.

The employment of a composition containing such adverse skin reaction preventing agents provides desensitization of the skin to the presence of skin-sensitizing agents as also encountered from transdermal systems before, after or during the transdermal administration of the therapeutic agent.

In another aspect of the present invention, the agents and compositions containing the same are also effective in preventing adverse responses caused by skin-irritating agents such as household and industrial cleansers, organic solvents and the like. These agents are effective in disrupting the inflammatory response by limiting the ability of the skin-irritating agent to elicit the neurologic, vascular and/or cellular phase of inflammation.

The above methods are useful for preventing skin sensitization or inflammation produced by a variety of skin-sensitizing agents such as, for example, a drug selected from, but not limited to, the following group: (a) an angiotensin converting enzyme inhibitor; (b) a beta adrenergic receptor blocker; (c) an anti-hypertensive drug other than an angiotensin converting enzyme inhibitor or a beta adrenergic receptor blocker; (d) an anti-histamine; (e) an anti-asthmatic; (f) a non-steroidal anti-inflammatory drug; (g) a central nervous system active drug; (h) a weight control drug; (i) an anticoagulant; a potassium control drug; (k) an immunomodulatory drug; (l) a decongestant; and (m) proteins and peptides such as insulin and thyrotropin-releasing hormone.

More specifically, the therapeutic agents for administration in accordance with the present invention include all of the major therapeutic areas, including, but not limited to: anti-infectives, such as antibiotics and antivitals; analgesics and analgesic combinations (such as capsaicin); anorexics; antiarthritics; anti-asthmatics (such as albuterol, metaproterenol, ketotifen and terbutaline); anticoagulants (such as urokinase); anticonvulsants; antidepressants; antidiabetics; antidiarrheals; antihistamines (such as chlorpheniramine and diphenhydramine); anti-inflammatory agents (such as ketoprofen, prostaglandins, flurbiprofen, diclofenac, indomethacin, piroxicam and ibuprofen); antimigrane agents; anti-motion sickness preparations; antinauseants; antineoplastics; antiparkinsonism drugs; antipruritics; antipsychotics; antipyretics; antispasmodics, including gastrointestinal and urinary; anticholinergics; sympathomimetics; xanthine derivatives; cardiovascular agents, including angiotensin converting enzyme inhibitors (such as captopril and fosinopril); beta blockers (such as nadolol, timolol, propranolol and alprenolol); antiarrythmics; antihypertensives (such as clonidine); vasodilators, including general, coronary, peripheral and cerebral; central nervous acting agents (such as fluphenazine, trifluoperazine, haloperidol, Xanax®, Librium®, Valium®); cough and cold preparations; decongestants; diagnostics; hormones; hypnotics; muscle relaxants; parasympatholytics; parasympathomimetics; psychostimulants; sedatives; weight control and appetite suppressive drugs (such as mazindol) and tranquilizers.

The above methods are also useful for preventing skin irritation produced by a variety of skin-irritating agents as previously described including but not limited to, eczema causing agents (e.g. rubber accelerators), household and industrial cleansers, water, organic solvents, oxidizing and/or reducing agents, alkalis, acids, oils, plant matter, animal matter and the like.

The present invention further provides an article useful for preventing the skin sensitizing or inflammatory effect of a component of a transdermal drug delivery system, where the component is either a drug, a skin permeation enhancer, or other materials or a combination of the same and the like, the article comprising:

(a) a transdermal delivery system comprising a therapeutic agent (e.g. a drug) of interest; and
(b) an effective amount of phenoxyacetic acid or lower alkyl ester thereof.

The adverse skin reaction preventing agents can also be administered in a transdermal or a controlled-release device. Examples of transdermal devices and delivery systems which may be used are disclosed in Bodde, H. E. et al., Crit. Rev. Ther. Drug Carrier Syst. 6:87–115 (1989); and in U.S. Pat. Nos. 3,598,122, 3,598,123, 4,286,592, 4,314,557, 4,379,454, 4,559,222, 4,573,995, which references are hereby incorporated by reference.

The delivery system may include a first transdermal device comprising a matrix for placing the adverse skin reaction preventing agents in transmitting relationship to the skin. A second transdermal device may be used to place the therapeutic agent in transmitting relationship to the skin after the adverse reaction preventing agent has been transdermally administered to the skin. The first and second transdermal devices may be incorporated into a single transdermal patch.

The adverse skin reaction preventing agents are administered by themselves, as part of a product applied to or coming into contact with the skin (e.g. shampoo), as part of a topical application composition (e.g. lotion, cream and the like) or in transdermal systems in combination with a therapeutic agent of interest. When administered alone, these agents may be administered topically or non-cutaneously such as intradermally, intravenously, intramuscularly, orally or intra-peritoneally. The agents of the present invention can be incorporated into a pharmaceutically acceptable composition for topical application to the skin in the form of lotions, creams gels and the like. Useful carriers for the preparations of such compositions include water, ethanol, gels and the like. The agents of the present invention may also be administered as part of a preparation (e.g. shampoo) which is applied to or in contact with the skin.

The precise formulation of the transdermally administered therapeutic agent (e.g. a drug) and the adverse skin reaction preventing agents of the present invention can be designed to deliver the drug and the agents at the desired fluxes and can be in numerous forms, including, without limitation, ointments, gels and creams. Aqueous formulations, in particular gels, typically comprise water and from about 1 to 2.5% (w/w) of a gelling agent such as hydroxyethylcellulose or hydroxypropylmethylcellulose (HPMC). Typical non-aqueous gels comprise silicone fluid or mineral oil. The mineral oil may also have from about 1 to 2% (w/w) of a gelling agent such as colloidal silicon dioxide. The suitability of a particular gel composition depends on the compatibility of its constituents with the drug (with or without a permeation enhancer) and the adverse skin reaction preventing agents.

In another embodiment, the agents of the present invention are delivered to the skin alone to prevent skin-sensitization and/or skin irritation or prior to the administration of the therapeutic drug or drugs. Such prior administration can be via transdermal application using a device as described above, via topical application, intracutaneous injection, and the like.

In yet another embodiment, the agents are delivered by another non-cutaneous route and method of delivery, either concurrently with, or prior to, the transdermal administration of the therapeutic drug.

In embodiments of the invention where the adverse skin reaction preventing agent is administered to prevent irritation of the skin, the composition containing the same is preferably in the form of a lotion, cream or other readily applied topical formulation.

In all of the above embodiments, the dosage of the adverse skin reaction preventing agents administered will be dependent upon the agent, the age, health, and weight of the recipient, kind of concurrent treatment, if any, and frequency of treatment.

The methods and compositions within the scope of this invention include all compositions and methods wherein the adverse skin reaction preventing agents are contained in an amount effective to achieve their intended purpose. While individual needs vary, determination of optimal ranges of effective amounts of each component is within the skill of the art.

For transdermal administration, typical effective dosages of the agents to prevent ACD by a sensitizing drug will depend on their permeation through human skin, and are a function of the physical properties of the permeant, including the partition coefficient of the permeant between solvent and skin, molecular weight and melting point. In general, the maximum flux that can be obtained from any permeant occurs from saturated solutions. Equations have been derived that predict accurately the maximum flux given the partition coefficient, molecular weight and melting point of the permeant as described in, for example, "TREATISE ON CONTROLLED DRUG DELIVERY", A. Kydonieus, ed., Marcel Dekker, Inc., N.Y., 1991, in particular, p. 370, equations 3a and 4a and p. 34, FIG. 2, incorporated herein by reference. For the transdermal delivery of phenoxyacetic acid and lower alkyl esters thereof, the expected maximum flux that can be delivered locally to skin is in the range of from about 1 to 50 $\mu g/c^2/hr$. These values are dependent, for example on varying skin age, skin type and skin condition. The preferred range for the maximum flux of the active ingredient is from about 5 to 25 $\mu g/cm^2/hr$. Accordingly, as will be understood by those skilled in the art, the delivery of a particular agent, is controlled by the percent saturation of that agent in the chosen vehicle.

The amount of phenoxyacetic acid and lower alkyl esters thereof which can be delivered to prevent ACD will vary from patient to patient. For example, the amount of the present agents delivered from a gel formulation (2.5% HPMC in 75% ethanol) is from about 0.1 to 10% by weight, and preferably from about 0.25% to 2.0% by weight.

For administration of the adverse skin reaction preventing agents to prevent skin irritation, the dosage will vary as described. For example for topical application, the amount of phenoxyacetic acid and lower alkyl esters thereof is from about 0.1 to 2.0 percent by weight, preferably from about 0.25 to 1.0 percent by weight based on the total weight of the composition.

When combined with a conventional product applied to or in contact with the skin, the amount of the active ingredient is typically from about 0.1 to 2.0 percent by weight of the total composition.

EXAMPLE 1

Phenoxyacetic Acid Methyl Ester As A Counter Sensitizer to DNCB

A 1.0% (w/v) solution of phenoxyacetic acid methyl ester (PAME, a compound of Formula I wherein R is methyl) was prepared in a gel formulation (2.5% HPMC in 75% ethanol). The same gel formulation served as a negative control. For sensitization, a 1% (w/v) solution of dinitrochlorobenzene (DNCB) was prepared in acetone.

Twenty-four (24) Balb/c mice had their back skin shaved. The mice were divided into three equal groups. The first group acted as a negative control and received on day 0 an application of acetone. The second and third groups each received 20 $\mu$L of 1% DNCB in acetone on the exposed back skin.

All three groups were challenged on the right ear with 20 $\mu$L of 1% DNCB in acetone five (5) days after sensitization. Then, 10 minutes after challenge, the first and second groups received 100 $\mu$L of 1% HPMC in 75% ethanol. The third group received 1% of PAME in the HPMC gel.

Adverse reaction to the challenge with DNCB was determined by measuring the thickness of the mice ears before and after challenge to determine the amount of swelling, and then comparing the degree of swelling for mice treated in accordance with the invention (Group III) with Groups I and Groups II. The results are shown in Table I.

TABLE I

| TREATMENT | EAR THICKNESS (MM × 10$^{-3}$) | EAR SWELLING (MM × 10$^{-3}$) | % SUPPRESSION |
|---|---|---|---|
| GROUP I NONE (HPMC GEL) | | | |
| 24 HOURS | 228 ± 3 | — | — |
| GROUP II DNCB ONLY (100 µg) | | | |
| 24 HOURS | 261 ± 13 | 33 | — |
| GROUP III PAME (1 MG) (IN HPMC GEL) (PRE ONLY) + DNCB (100 µg) | | | |
| 24 HOURS | 240 ± 6 | 12 | 62 |

As shown in Table I, the Group II mice exhibited significant ear swelling when sensitized to DNCB. Phenoxyacetic acid methyl ester when administered alone prevented an adverse reaction of the skin induced by sensitization with DNCB when administered prophylactically.

EXAMPLE 2

Phenoxyacetic Acid Methyl Ester As A Counter Sensitizer to Oxazolone

The procedures of Example 1 were repeated except that the mice were sensitized with a 1% (w/v) solution of oxazolone. The results are shown in Table II.

TABLE II

| TREATMENT | EAR THICKNESS (MM × 10$^{-3}$) | EAR SWELLING (MM × 10$^{-3}$) | % SUPPRESSION |
|---|---|---|---|
| NONE (HPMC GEL) | | | |
| 24 HOURS | 262 ± 6 | — | — |
| OXAZOLONE ONLY (100 µg) | | | |
| 24 HOURS | 368 ± 25 | 106 | — |
| PAME (2 mg) (in HPMC GEL) + OXAZOLONE (100 µg) | | | |
| 24 HOURS | 278 ± 15 | 16 | 84 |

As shown in Table II, the Group II mice showed significant ear swelling when sensitized with oxazolone. PAME constituting an adverse skin reaction preventing agent in accordance with the present invention suppressed adverse reactions induced by sensitization with oxazolone.

EXAMPLE 3

Phenoxyacetic Acid Methyl Ester Inhibits Irritation Induced by Captopril

Thirty (30) Balb/c female mice were obtained from Sprague Dawley Labs. A 1.0% (w/v) solution of PAME was prepared in a gel formulation (2.5% HPMC in 75% ethanol). A second solution containing a 2:1 volume ratio of acetone to ethanol was also prepared. A 20% (w/v) solution of captopril and the second solution (sufficient to elicit a strong irritant response), was also prepared. In addition a 1.0% HPMC solution was prepared as a placebo.

The Group I mice (10 mice) received the second solution and then 10 minutes later the HPMC solution. The positive control mice (10) designated as Group II received the captopril solution to the right ear followed by the HPMC solution. The experimental group of mice (10) (Group III) received the captopril solution to the right ear followed ten minutes later by the PAME solution.

The thickness of the ears was measured after 2 hours when maximum redness and swelling from the captopril solution were observed. The results are shown in Table III.

TABLE III

| TREATMENT | EAR THICKNESS (MM × 10$^{-3}$) | % SUPPRESSION |
|---|---|---|
| GROUP I NONE (HPMC GEL) | | |
| 2 HOURS | 224 ± 7 | — |
| GROUP II CAPTOPRIL ONLY | | |
| 2 HOURS | 250 ± 17 | — |
| GROUP III PAME + CAPTOPRIL | | |
| 2 HOURS | 226 ± 5 | ≈93 |

As shown in Table III, the Group II mice exhibited significant ear swelling when contacted with captopril. PAME constituting an adverse skin reaction preventing agent suppressed inflammation induced by contact with captopril.

EXAMPLE 4

Phenoxyacetic Acid Methyl Ester Inhibits Irritation Induced by Retinoic Acid

The procedures of Example 3 were repeated except that captopril was replaced by retinoic acid in an amount of 1% (w/v) in a 1% HPMC gel. The results are shown in Table IV.

TABLE IV

| TREATMENT | EAR THICKNESS (MM × 10$^{-3}$) | % SUPPRESSION |
|---|---|---|
| GROUP I NONE (HPMC GEL) | | |
| 2 HOURS | 239 ± 4 | — |
| GROUP II RETINOIC ACID ONLY | | |
| 2 HOURS | 273 ± 19 | — |
| GROUP III PAME + RETINOIC ACID | | |
| 2 HOURS | 237 ± 11 | 100 |

As shown in Table IV, the Group II mice exhibited significant ear swelling when contacted with retinoic acid. PAME constituting an adverse skin reaction preventing agent suppressed inflammation induced by retinoic acid.

EXAMPLE 5

Phenoxyacetic Acid and Phenoxyacetic Acid Methyl Ester Inhibits Irritation Induced By Phorbol Myristate The procedures of Example 4 were repeated except that captopril was replaced with phorbol myristate (12-tetradecanyol-13-phorbol myristic acid) in an amount of 0.1% (w/v) in a 1% HPMC gel. Phenoxyacetic acid was also tested in this protocol. The results are shown in Table V.

TABLE V

| TREATMENT | EAR THICKNESS (MM × 10⁻³) | % SUPPRESSION |
|---|---|---|
| GROUP I NONE (HPMC GEL) 2 HOURS | 226 ± 4 | — |
| GROUP II PHORBOL MYRISTATE ONLY 2 HOURS | 265 ± 14 | — |
| GROUP III PAME + PHORBOL MYRISTATE 2 HOURS | 234 ± 9 | ≈80 |
| GROUP IV PHENOXYACETIC ACID + PHORBOL MYRISTATE 2 HOURS | 239 ± 8 | ≈67 |

As shown in Table V, the Group II mice exhibited significant ear swelling when contacted with phorbol myristate. PAME and phenoxyacetic acid constituting adverse skin reaction preventing agents suppressed inflammation induced by contact with phorbol myristate.

EXAMPLE 6

Phenoxyacetic Acid Methyl Ester Inhibits Irritation Induced By Dinitrochlorobenzene The procedures of Example 4 were repeated except that captopril was replaced with dinitrochlorobenzene (DNCB) in an amount of 2.0% (w/v) in a 1% HPMC gel. The results are shown in Table VI.

TABLE VI

| TREATMENT | EAR THICKNESS (MM × 10⁻³) | % SUPPRESSION |
|---|---|---|
| GROUP I NONE (HPMC GEL) 2 HOURS | 249 ± 11 | — |
| GROUP II DNCB ONLY 2 HOURS | 277 ± 11 | — |
| GROUP III PAME + DNCB 2 HOURS | 249 ± 8 | 100 |

As shown in Table VI, the Group II mice exhibited significant ear swelling when contacted with dinitrochlorobenzene (DNCB). PAME constituting an adverse skin reaction preventing agent suppressed inflammation induced by contact with DNCB.

What is claimed is:

1. A method of preventing an adverse reaction of the skin of a warm-blooded animal to the presence of at least one of a skin-sensitizing agent or a skin-irritating agent comprising administering to said warm-blooded animal an amount of an adverse skin reaction preventing agent sufficient to prevent said adverse reaction, said adverse skin reaction preventing agent comprising phenoxyacetic acid or a lower alkyl ester thereof.

2. The method of claim 1 wherein the skin-sensitizing agent is selected from the group consisting of therapeutic agents, metals, fragrances, cosmetics, textiles, pollen, pesticides, plastics and combinations thereof.

3. The method of claim 1 wherein the skin-irritating agent is selected from the group consisting of water, cleansers, eczema causing agent, alkalis, acids, oils, organic solvents, oxidizing agents, reducing agents, plant matter, animal matter and combinations thereof.

4. The method of claim 1 comprising administering said adverse skin reaction preventing agent topically to the skin.

5. The method of claim 4 where said adverse skin reaction preventing agent is administered transdermally.

6. The method of claim 5 wherein the skin-sensitizing agent or skin-irritating agent is a therapeutic agent, said method comprising administering said adverse skin reaction preventing agent and the therapeutic agent from a transdermal patch.

7. The method of claim 4 wherein said adverse reaction skin preventing agent is incorporated into a product applied to or in contact with the skin.

8. The method of claim 6 wherein said product is a hair treatment preparation, a hand lotion, a soap, a cleanser, and a detergent.

9. The method of claim 1 wherein the phenoxyacetic acid ester is phenoxyacetic acid methyl ester.

10. The method of claim 5 wherein the maximum flux of the adverse skin reaction preventing agent is from about 1 to 50 µg/cm²/hr.

11. The method of claim 10 wherein the maximum flux of the adverse skin reaction preventing agent is from about 5 to 25 µg/c²/hr.

12. The method of claim 1 comprising administering to the warm-blooded animal an amount of said adverse skin reaction preventing agent sufficient to prevent allergic contact dermatitis caused by a skin-sensitizing agent in the form of a gel, said amount of the adverse skin reaction preventing agent being from about 0.1 to 10% by weight.

13. The method of claim 12 wherein the amount of the adverse skin reaction preventing agent is from about 0.25 to 2.0% by weight.

14. A transdermal delivery system for transdermally administering an amount of an adverse skin reaction preventing agent sufficient to prevent said adverse reaction, said adverse skin reaction preventing agent comprising phenoxyacetic acid or a lower alkyl ester thereof, said system comprising:

(a) a first transdermal device comprising a matrix for placing the adverse skin reaction preventing agent in transmitting relationship to the skin; and (b) a second transdermal device comprising a matrix for placing a therapeutic agent in transmitting relationship to the skin after the adverse skin reaction preventing agent has been transdermally administered to the skin from the first transdermal device.

15. The transdermal delivery system of claim 14 wherein the first and second transdermal devices are contained within a single transdermal patch.

16. A method of transdermally administering to a warm-blooded animal a therapeutic agent without thereby eliciting an adverse reaction from the skin from any source comprising transdermally administering to said warm-blooded animal before, after or during the administration of the therapeutic agent an amount of an adverse skin reaction preventing agent sufficient to prevent said adverse reaction, said adverse skin reaction preventing agent comprising phenoxyacetic acid or lower alkyl ester thereof.

17. The method of claim 16 wherein the phenoxyacetic acid lower alkyl ester is phenoxyacetic acid methyl ester.

* * * * *